United States Patent
Lentz et al.

(10) Patent No.: US 7,815,762 B2
(45) Date of Patent: Oct. 19, 2010

(54) METHOD OF FORMING AN INTRODUCER SHEATH

(75) Inventors: David Christian Lentz, Bloomington, IN (US); William L. Howat, Laconia, NH (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 12/198,500

(22) Filed: Aug. 26, 2008

(65) Prior Publication Data

US 2010/0057018 A1    Mar. 4, 2010

(51) Int. Cl.
- B29C 65/00 (2006.01)
- B29C 49/00 (2006.01)
- B32B 37/00 (2006.01)
- B65C 3/16 (2006.01)
- C08J 5/00 (2006.01)
- A61M 25/00 (2006.01)

(52) U.S. Cl. .......... 156/84; 156/198; 156/215; 156/294; 156/308.2; 604/524

(58) Field of Classification Search ............ 156/84, 156/85, 86, 196, 198, 212, 213, 215, 221, 156/293, 294, 308.2, 308.4, 309.6; 604/264, 604/523, 524, 525, 526, 527
See application file for complete search history.

(56) References Cited

U.S. PATENT DOCUMENTS

| | | | |
|---|---|---|---|
| 3,861,972 A * | 1/1975 | Glover et al. ............. 156/86 |
| 4,269,640 A * | 5/1981 | Ruiz et al. ............... 156/84 |
| 5,240,537 A * | 8/1993 | Bodicky ............... 156/244.13 |
| 5,380,304 A * | 1/1995 | Parker ................... 604/526 |
| 5,514,236 A * | 5/1996 | Avellanet et al. ......... 156/154 |
| 5,811,043 A * | 9/1998 | Horrigan et al. ......... 264/138 |
| 5,863,366 A * | 1/1999 | Snow .................... 156/143 |
| 5,951,539 A * | 9/1999 | Nita et al. ............... 604/526 |
| 6,702,972 B1 * | 3/2004 | Markle .................. 264/230 |
| 6,939,337 B2 | 9/2005 | Parker et al. ............ 604/528 |
| 2001/0034514 A1 * | 10/2001 | Parker ................... 604/525 |
| 2004/0068287 A1 * | 4/2004 | Lim et al. ............... 606/194 |
| 2007/0276354 A1 * | 11/2007 | Osborne ................. 604/527 |

* cited by examiner

Primary Examiner—Richard Crispino
Assistant Examiner—Brian R Slawski
(74) Attorney, Agent, or Firm—Brinks Hofer Gilson & Lione

(57) ABSTRACT

A method of forming an introducer sheath having a crease-free tapered distal tip portion. A mandrel is provided having an outer configuration comprising an elongated body and a tapered distal tip portion. A generally tubular inner liner comprising heat shrinkable PTFE, is positioned over the mandrel. The inner liner is heat shrunk to the outer configuration of the mandrel, in a manner that avoids the formation of creases along the inner diameter of the liner. A reinforcing member is positioned over a length of the inner liner, and an outer jacket is positioned over the reinforcing member and the inner liner. The liner, reinforcing member, and outer jacket are heated in a heat shrink enclosure, whereby the outer jacket melts and bonds to an outer surface of the inner liner.

8 Claims, 4 Drawing Sheets

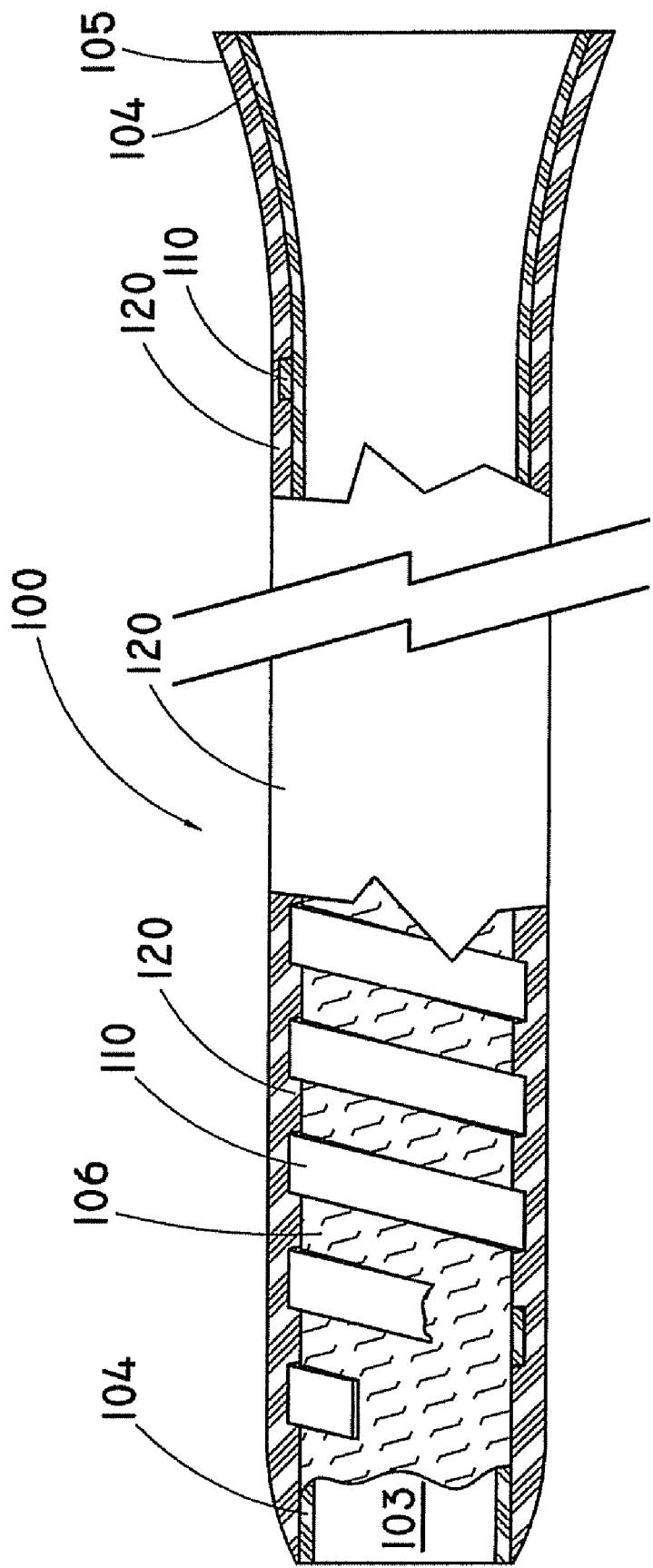

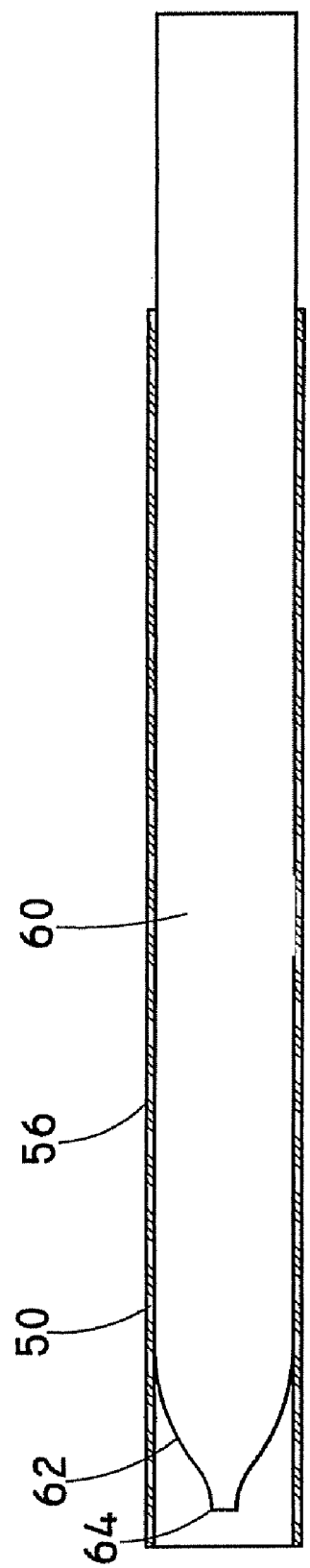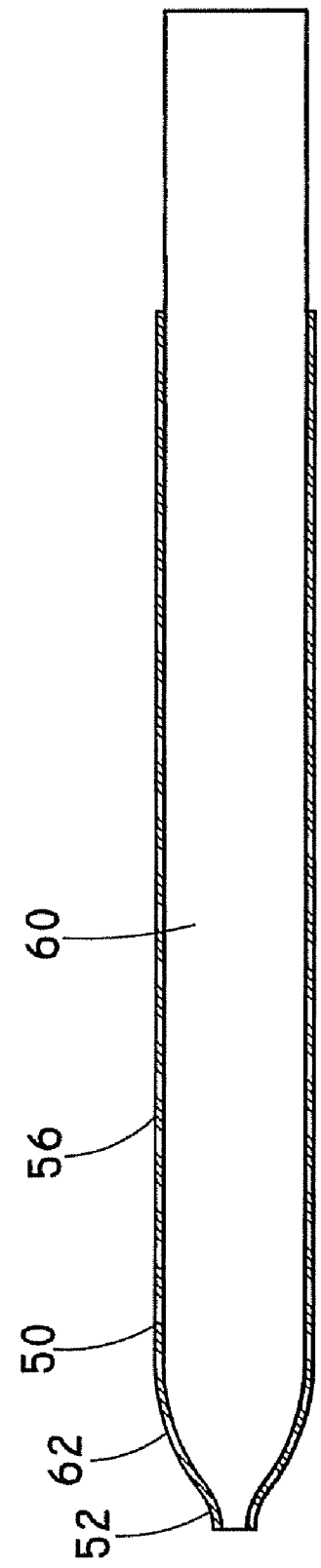

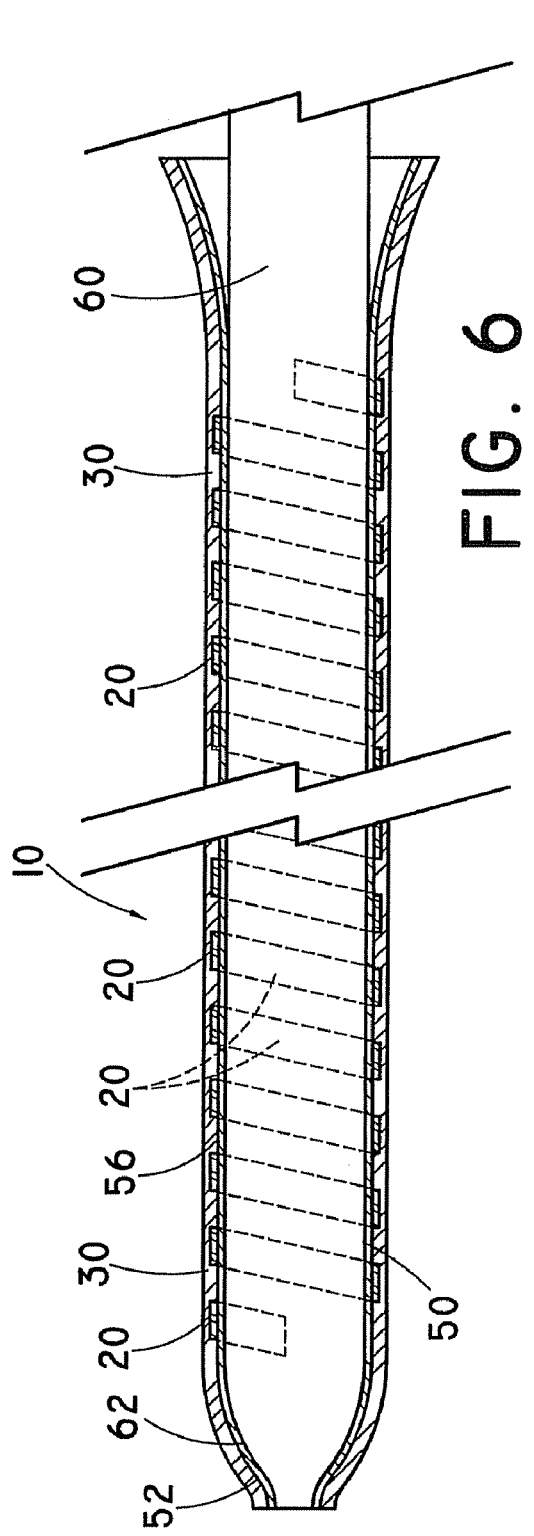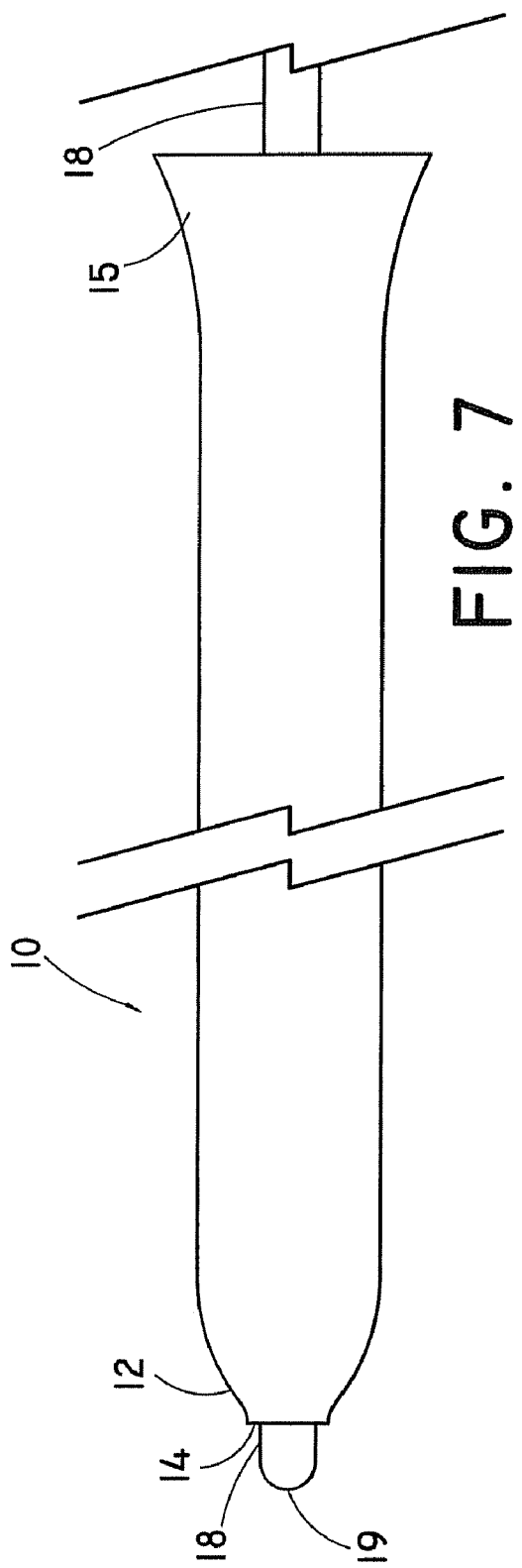

METHOD OF FORMING AN INTRODUCER SHEATH

BACKGROUND

1. Technical Field

This invention relates to the field of medical introducer apparatuses. More particularly, the invention relates to a method of forming an introducer sheath, and to an introducer sheath having a crease-free inner diameter formed by the inventive method.

2. Background Information

Numerous advances of considerable note have occurred in medical surgical techniques over the last few decades. Among the most significant advances has been the adoption, and now-routine performance, of a variety of minimally invasive procedures. Such procedures include angioplasty, endoscopy, laparoscopy, and arthroscopy, as well as numerous other diagnostic and therapeutic operations. These minimally invasive procedures can be distinguished from conventional open surgical procedures in that access to a site of concern within a patient is achieved through a relatively small incision, into which a tubular device (or tubular portion of a device) is inserted or introduced. The tubular device, or device portion, keeps the incision open while permitting access to the target site via the interior (i.e., the lumen) of the tube.

Body passageways in which introducer apparatuses have been used to introduce medical interventional devices and/or liquid medicaments include the esophagus, trachea, colon, biliary tract, urinary tract, and virtually all portions of the vascular system, among others. One particularly significant example of a minimally invasive technique involves the temporary or permanent implantation of a medical interventional device, such as a stent, into a body passageway of a patient. Other examples involve the transmission of a liquid medicament to a target area, and/or the withdrawal of body fluid from the body passageway.

When carrying out these, and other, desired techniques, communication with the passageway is typically attained by inserting an access device, such as an introducer sheath, into the body passageway. One typical procedure for inserting the introducer sheath is the well-known Seldinger percutaneous entry technique. In the Seldinger technique, a needle is initially injected into the passageway, such as a vessel, and a wire guide is inserted into the vessel through a bore of the needle. The needle is withdrawn, and an introducer assembly is inserted over the wire guide into the opening in the vessel.

Typically, the introducer assembly includes an outer introducer sheath, and an inner dilator having a tapered distal end. The tapered end of the dilator stretches the opening in the vessel in controlled fashion, so that introduction of the larger diameter introducer sheath may then be carried out with a minimum of trauma to the patient. Following satisfactory placement of the introducer sheath, the dilator is removed, leaving at least the distal portion of the larger diameter introducer sheath in place in the vessel. The interventional device, such as a stent, etc., or the liquid medicament may then be passed through the introducer sheath for delivery to the target site.

Historically, percutaneous insertion techniques were problematic, due in large part to the lack of flexibility and/or kink resistance of the sheath. Early sheaths were generally formed of a relatively stiff fluoropolymer, such as polytetrafluoroethylene (PTFE) or fluorinated ethylene propylene (FEP). The sheaths were typically of thin-walled construction, and were prone to kinking, particularly when threaded through tortuous pathways within the body. Increasing the thickness of the sheath only minimally improved the kink resistance of the sheath. At the same time, the added thickness occupied valuable space in the vessel, thereby minimizing the diameter of the interventional device that could be passed therethrough. In addition, increasing the thickness of the sheath necessitated the use of a larger entry opening than would otherwise be required.

A kinked sheath is essentially unusable, and generally cannot be straightened while positioned in the body of the patient. Consequently, once a sheath kinks, the sheath must be removed, leaving an enlarged, bleeding opening which typically cannot be reused. Access to the vessel must then be re-initiated at an alternative site, and the process repeated with a new sheath. In many cases, a suitable alternative site is not available, and the percutaneous procedure must be abandoned altogether in favor of a different, and often more intrusive, technique.

In recent years, introducer sheaths have been improved in order to enhance their flexibility and kink resistance. Such sheaths are now routinely used to percutaneously access sites in the patient's anatomy that previously could not be accessed with existing sheaths, or that could be accessed only upon the exercise of an undesirable amount of trial and error, with the concomitant discard of sheaths whose placement had been unsuccessful.

Many newer sheaths exhibit a much higher degree of kink resistance than was achievable with prior art sheaths. One example of a flexible, kink resistant introducer sheath is described in U.S. Pat. No. 5,380,304. The sheath described in this patent includes a lubricious inner liner having a helical coil fitted over the liner. An outer tube is connected to the outer surface of the liner through the coil turns. The coil reinforcement imparts kink resistance to this thin-walled sheath through a wide range of bending.

U.S. Patent Publication No. 2001/0034514 discloses an introducer sheath similar in many respects to the sheath of the '304 patent. The sheath in the patent publication is formed such that the proximal end of the sheath has a higher stiffness, while the distal end has a lower stiffness. Since the distal portion of the sheath has a lower stiffness (and therefore is more flexible) than the proximal portion, the sheath is able to traverse portions of the anatomy that would have been difficult, if not impossible, to traverse with stiffer sheaths. Since the proximal portion has a higher stiffness (and is therefore less flexible) than the distal portion, the sheath maintains the trackability to traverse tortuous areas of the anatomy. This presence of the coil reinforcement also enables this sheath to be kink resistant through a wide range of bending angles.

U.S. Pat. No. 6,939,337 discloses a sheath having a coil reinforcement, as well as a braid reinforcement positioned over (i.e., radially outwardly of) at least a length of the coil. This sheath utilizes a coil for the purposes of providing kink resistance in the same manner as the '304 patent and the patent publication recited above, and also includes a braid to enhance torqueability and pushability of the sheath. Each of the patent references cited above is incorporated herein by reference.

The development of introducer sheaths, such as those described above, has revolutionized the practice of medicine. In particular, this development has enhanced the ability of the physician to introduce medical interventional devices and liquid medicaments into target sites that had previously been difficult, if not impossible, to reach without the necessity of carrying out much more intrusive open surgical operations. The percutaneous methods described are generally less expensive than the open surgical methods previously employed, are less traumatic to the patient, and typically require a shorter patient recovery time.

Notwithstanding the benefits that have been achieved by the use of such introducer sheaths, new challenges continue to be faced. For example, as noted above, introducer sheaths are frequently introduced into the body passageway in combination with a tapered inner dilator. In many cases, the introducer sheath is provided with a tapered distal end that corresponds, in some fashion, to the taper of the dilator. This relationship is intended to minimize the transition between the dilator and introducer sheath upon insertion of the sheath through the percutaneous opening, thereby further minimizing the trauma experienced by the patient upon insertion.

Many typical introducer sheaths, such as the sheaths described in the incorporated-by-reference patents, may include a lubricious inner liner formed of a relatively stiff fluoropolymer, such as PTFE. The reinforcement, e.g., the coil and/or braid, is fitted over the liner, and the outer tube, formed of a more flexible polymer, such as a polyether block amide, nylon, or polyurethane is fitted over the liner. The entire assembly is typically placed in a heat shrink enclosure, and heated in an oven. The outer surface material melts and bonds to the outer surface of the inner liner through the coil turns, or the filaments of the braid.

Typically, such sheaths have a constant, or substantially constant, inner diameter extending virtually the entire length of the sheath, from the proximal end to the distal tip area. However, as stated above, in some cases it is desired to taper the distal tip to correspond to the taper of the dilator. In this event, the distal tip portion of the sheath is generally placed in a heated die that gradually reduces the diameter of the distal tip to the desired taper. Since the inner liner is generally formed of a higher melting material (e.g., PTFE) when compared to the material of the outer jacket (e.g., a polyether block amide), the liner does not melt flow in the die in the nature of the outer jacket under the conditions in the die. As a result, as the diameter of the sheath decreases upon tapering, creases or wrinkles are prone to form along the inner diameter of the liner.

It is desired to overcome the problems of the prior art by providing a method of forming an introducer sheath having a tapered distal tip formed by the inventive method, wherein the inner diameter of the sheath is substantially free of wrinkles and creases at the tapered distal tip portion. It is also desired to provide an introducer sheath having an inner liner substantially free of wrinkles and creases.

BRIEF SUMMARY

The problems of the prior art are addressed by the method and device of the present invention.

In one form thereof, the invention comprises a method of forming an introducer sheath having a tapered distal tip portion. A mandrel is provided having an outer configuration comprising an elongated body and a tapered distal tip portion. A generally tubular inner liner comprising a heat shrinkable fluoropolymer, such as PTFE, is positioned over the mandrel. The inner liner is heat shrunk to the outer configuration of the mandrel, in a manner such that the inner diameter of at least the distal end of the liner is free of creases. A reinforcing member is positioned over a length of the inner liner, and an outer jacket is positioned over the reinforcing member and the inner liner. This assembly is heated in a heat shrink enclosure such that the outer jacket melts and bonds to an outer surface of the inner liner.

In another form thereof, the invention comprises a method of forming an introducer sheath. A mandrel having an elongated body and a tapered distal tip portion is provided. A polymeric tubular liner having a first melt temperature is heat shrunk to the outer configuration of the mandrel. An outer jacket having a second melt temperature, less than the first melt temperature, is heat shrunk over the liner. A reinforcing member may be positioned between the liner and the outer jacket.

In yet another form thereof, the invention comprises an introducer sheath. An inner liner has a proximal end and a distal end, and has an inner diameter and an outer diameter. The inner and outer diameters taper to a distal tip portion that is free of creases. A reinforcing member is positioned over the inner liner, and an outer jacket is positioned over the inner liner and the reinforcing member. The outer jacket has a proximal end and a distal end, and an inner diameter and an outer diameter. The inner and outer diameters taper to a distal tip portion of the outer jacket. The outer jacket is bonded to the outer diameter of the inner liner.

BRIEF DESCRIPTION OF THE DRAWINGS

FIG. 3 is a partially sectioned view of the prior art introducer sheath of FIG. 1 after heating, following the removal of the mandrel and heat shrink tube;

FIG. 4 is a longitudinal sectional view of a heat shrinkable inner liner tube fitted over a mandrel, prior to shrinkage;

FIG. 5 is a longitudinal sectional view of the heat shrinkable inner liner tube of FIG. 4 fitted over the mandrel following shrinkage of the distal tip portion;

FIG. 6 is a longitudinal sectional view of one embodiment of an introducer sheath formed according to the inventive method, shown positioned over a mandrel; and FIG. 7 is a side view of an introducer sheath formed according to the present invention, and illustrates a dilator extending through the inner diameter of the sheath.

DETAILED DESCRIPTION OF THE DRAWINGS AND THE PRESENTLY PREFERRED EMBODIMENTS

Figure 1:
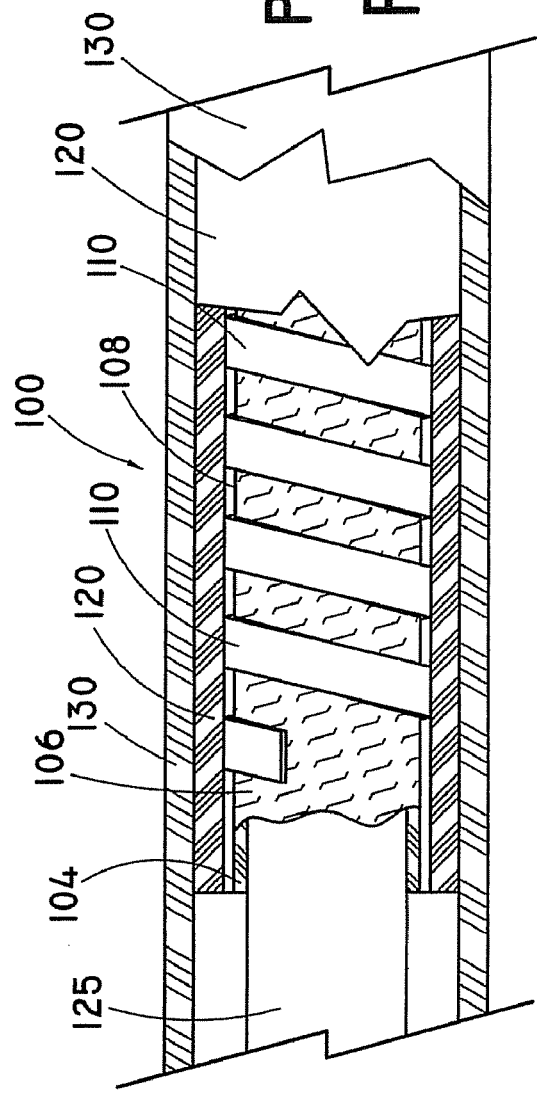
FIG. 1 is a partially sectioned view of a prior art introducer sheath prior to heating, the sheath being positioned over a mandrel and having a heat shrink tube positioned thereover.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

In the following discussion, the terms "proximal" and "distal" will be used to describe the opposing axial ends of the inventive sheath, as well as the axial ends of various component features. The term "proximal" is used in its conventional sense to refer to the end of the sheath (or component thereof) that is closest to the operator during use of the sheath. The term "distal" is used in its conventional sense to refer to the end of the sheath (or component thereof) that is initially inserted into the patient, or that is closest to the patient during use.

It is now well-known to form an introducer sheath by heat shrinking an outer polymeric layer onto an inner liner formed of a lubricious material, such as a fluoropolymer. When a reinforcing member, such as a coil or a braid, is to be included in the sheath, the outer polymeric jacket is heat shrunk onto the roughened outer surface of the inner liner through the turns of the coil, or the filaments of the braid.

Figure 2:
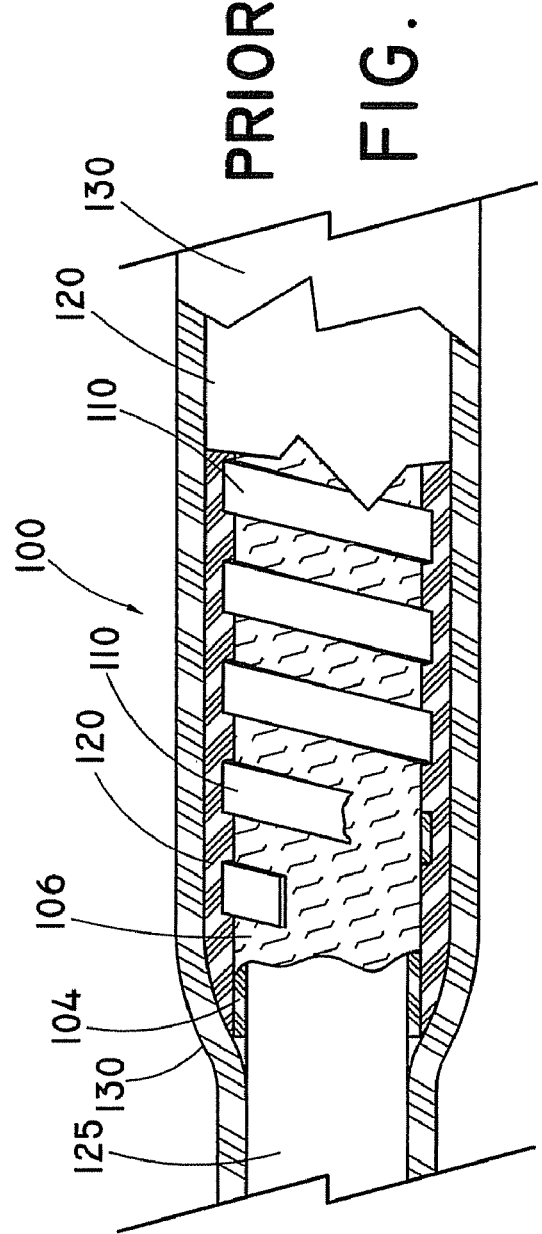
FIG. 2 is a partially sectioned view of the prior art introducer sheath of FIG. 1 after heating.

FIGS. 1 and 2 depict a partially sectioned view of a sheath undergoing formation by a prior art process, in this case, the heat shrink process described in U.S. Pat. No. 5,380,304. In this non-limiting example, the sheath includes a flat wire helical coil reinforcement. The introducer sheath being formed includes an inner liner 104 formed of the fluoropolymer PTFE, a flat wire coil reinforcement 110, and an outer polymeric jacket 120. An elongated mandrel 125 of constant outer diameter extends through the inner liner. The outer diameter of the mandrel is substantially the same as, or slightly larger than, the inner diameter of the liner. A heat shrink tube 130 is positioned over outer jacket 120.

FIG. 1 illustrates the relative position of the sheath components prior to heat shrinking in the oven. Due to the presence of the coil radially positioned between the inner liner 104 and the outer polymeric jacket 120, a longitudinal space 108 extends between the inner liner and the outer jacket. FIG. 2 illustrates the components after heating in the oven. As may be observed in FIG. 2, the outer polymeric jacket 120 has melted and flowed into this longitudinal space, and bonded to the outer surface 106 of the inner liner 104 between the spaces of the coil. Outer surface 106 has previously been roughened by conventional procedures, such as chemical etching, to enhance the strength of the bond. Heating the entire assembly "shrinks" the heat shrink tube, such that a radial force is exerted on melted outer jacket 120 to effect the configuration shown in FIG. 2.

Following the heat shrink application, the mandrel is removed and the heat shrink tube is cut away from the sheath. One example of a prior art introducer sheath 100 resulting from this process is shown in FIG. 3. If desired, an extended distal tip may be applied to the sheath. Due to the presence of the elongated mandrel about which the sheath is heated, the resulting prior art sheath is provided with a passageway 103 having an inner diameter that is substantially constant from one end of the sheath to the other. If desired, the proximal end 105 can be flared by well-known means.

In some instances, it is desirable to provide a sheath having a tapered distal tip portion, and a tapered inner diameter formed thereby in the distal direction. Having a taper at the distal tip portion provides a generally smooth transition between the respective outer diameters of the distal end of the sheath and the tapered dilator. This arrangement facilitates entry of the dilator and sheath into the body passageway in substantially non-traumatic fashion.

In order to form a taper on a prior art sheath such as that described above, the distal tip of the sheath is typically inserted into a suitably-shaped heated die. Upon heating, the distal tip assumes the particular shape imparted in the die. When in the die, the lower melting outer polymer (e.g., polyether block amide, nylon, polyurethane) melts, and is formed into the desired shape. Under normal heat shrink conditions for forming such sheaths, the higher melting inner liner (e.g., PTFE) does not melt flow under the conditions in the die. As the inner liner material is shape-compressed in the die to form the smaller diameter taper, the excess liner material not needed for the taper results in the formation of wrinkles or creases along this length of the liner.

The inner diameter of the fluoropolymer material of the inner liner is typically very lubricious (i.e., slippery), and has a low coefficient of friction. As a result, this surface allows passage therethrough of the medical interventional device and/or fluid with a minimum of resistance. However, the presence of wrinkles or creases may be disruptive of such free passage or flow in some instances. Surfaces may be created that obstruct the passage of the interventional device, or that may be susceptible to clotting or otherwise hindering the free flow of fluids. Desirably, the inner diameter of such sheaths would be structured such that the smooth texture of the inner diameter extends the length of the sheath, without the presence of such wrinkles or creases at the tapered distal portion of the sheath.

The inner diameter of the liner of the sheath formed by the inventive method avoids the wrinkles or creases that may otherwise be present in the prior art sheaths. Unlike the prior art structure, in this case, the fluoropolymer used as the inner liner, such as PTFE, has been suitably treated to impart heat shrink recovery properties to the inner liner. Such properties enable the inner liner to shrink upon application of heat to assume the shape of the underlying substrate (mandrel). Heat shrink fluoropolymers are known in the art, and are commonly employed over a substrate for abrasion protection, waterproofing, and for the application of a tight, protective coating to the substrate.

Those skilled in the art will appreciate that heat shrinkable PTFE tubing may be formed by radially expanding, or stretching, a tubular length of PTFE to an inner diameter of, for example, about two to four times the inner diameter of the original PTFE tube. The radially stretched tube is then placed on a mandrel, and exposed to heat and pressure. Upon cooling of the tube and removal of the mandrel, the PTFE tube retains the new, expanded inner diameter. Those skilled in the art can determine an appropriate amount of heat and pressure required to expand a particular fluoropolymer taking into consideration factors such as the melting point of the fluoropolymer, and the thickness and configuration of the tube.

Heat shrink fluoropolymers are capable of shrinking to recover their original diameter, or alternatively, shrinking to the diameter of an underlying substrate (such as a mandrel), upon exposure to heat. The amount of heat necessary to initiate shrinkage will, once again, vary with the particular fluoropolymer, and is also dependent upon factors such as the thickness and configuration of the tube. Most fluoropolymers, however, have a shrinkage temperature within a general range for that particular fluoropolymer. Heat shrink PTFE, for example, typically shrinks at a temperature of about 650° F. (340° C.). Heat shrink FEP typically recovers its original diameter at a temperature of about 420° F. (215° C.).

In addition to forming heat shrinkable fluoropolymer tubing by known means, such tubing may also be obtained from commercial sources. One such source is Zeus Industrial Products, Inc., of Orangeburg, S.C. Commercial vendors are typically capable of providing fluoropolymer heat shrink tubing in a variety of lengths, thicknesses and diameters, and that has a shrink temperature appropriate for the intended use.

The inventive method for forming an introducer sheath will now be described. An important feature of the inventive method is the use of an inner liner formed of a heat shrinkable fluoropolymer tube. The use of the heat shrinkable fluoropolymer liner enables the liner to shrink upon application of heat, thereby forming a tight fit wherein the fluoropolymer assumes the shape of a mandrel inserted through the fluoropolymer tube.

FIG. 4 is a sectional view of a heat shrink fluoropolymer tube 50 positioned over a mandrel 60. Tube 50 is of a conventional wall thickness for use as an inner liner in an introducer sheath, such as about 0.0005 to about 0.003 inch (0.013 to 0.076 mm). The inner diameter of tube 50 is also of conventional size for an introducer sheath, such as between about 4 and 20 French.

The lubricious PTFE material presents a slippery inner surface to allow easy insertion and withdrawal of the medical interventional device. The inner surface is also smooth and nonporous for minimizing the formation of blood clots and other thrombi thereon. The wall of the inner liner 50 has sufficient radial rigidity to prevent the reinforcing member (such as a coil) from protruding into the inner sheath passageway.

Mandrel 60 is typically formed of a material, such as stainless steel, that is capable of withstanding the temperatures utilized for shrinking tube 50, as described herein. The mandrel will have been pre-shaped by conventional means, such as grinding, laser cutting, etc., such that its outer diameter has a tapered distal tip 62 that tapers to distal end 64. Mandrel tapered tip 62 and distal end 64 may be formed to have any tapered configuration desired, which configuration will typically be selected based upon the particular tapered configuration desired for the resulting sheath.

FIG. 5 illustrates inner liner tube 50 following the application of heat. If liner 50 is formed of heat shrinkable PTFE, the tube and mandrel are placed in an oven and exposed to a temperatures of about 650° F. (340° C.). As illustrated, the distal portion 52 of tube 50 shrinks to assume the configuration of the mandrel. Utilizing the heat shrink tube composition enables the inner diameter of distal portion 52 to taper as shown so that it tightly conforms to the shape of the mandrel, thereby avoiding the formation of wrinkles or creases that might otherwise be formed if the liner was not capable of heat shrinking along the mandrel.

Following preparation of the inner liner 50 as described, introducer sheath 10 may now be assembled. Those skilled in the art will appreciate that many techniques are available for forming a sheath, such as the sheaths described in the incorporated-by-reference patent documents. Many of these techniques may be appropriate for use with the tapered liner described above.

FIG. 6 depicts a longitudinal cross-sectional view of one embodiment of introducer sheath 10 formed according to the inventive method, shown positioned over mandrel 60. As illustrated, introducer sheath 10 includes inner liner 50, a reinforcing member 20 fitted around inner liner 50, and a polymeric outer jacket 30 mechanically connected to a roughened outer surface 56 of inner liner 50.

Once the tapered distal tip 52 of inner liner (tube) 50 as shown in FIG. 5 is formed, the mandrel and liner 50 are cooled, whereupon the mandrel and liner are ready for further processing. The reinforcing member (e.g., a coil and/or a braid) may be wrapped, compression fitted, or otherwise positioned over the cooled inner liner and mandrel in any well known manner. Sheath reinforcing members, such as coils and braids, are well known in the medical arts. Reinforcing members are typically formed of many possible compositions (such as metals, metal alloys, etc.) and can be formed herein to have virtually any cross-sectional shape, thickness, pitch, compression, etc., common in the art. For purposes of illustration only, the following discussion describes the use of a flat wire coil reinforcement 20 having a generally constant pitch, and uniform spacing between adjacent coil turns. Further details of the use and placement of reinforcements in an introducer sheath are also provided in the incorporated-by-reference patent documents.

The tubular outer jacket 30 is then slid or otherwise positioned over the coil 20. This step is similar to that illustrated in FIG. 1, wherein reference is made to the formation of the prior art sheath depicted in that figure. Once again, the outer jacket can be formed of any material (e.g., an extrudable thermoplastic material such as polyether block amide, nylon, or polyurethane) commonly used for such purposes in the medical arts, and that is capable of melting as described herein. When outer jacket 30 is positioned as described, the entire assembly comprising the mandrel 60, inner liner 50, coil 20 and outer jacket 30 is placed in a heat shrink enclosure, such as FEP, and oven heated to a temperature of, for example, about 365° F. (185° C.). As the heat shrink enclosure shrinks upon the application of heat, the heated outer jacket 30 melts. Outer jacket 30 is then compressed by the shrinking FEP enclosure between the turns of the coil 20 to mechanically connect with roughened surface 56 of inner liner 50. The heat formable outer jacket material is self-leveling, which provides a uniform outer diameter surface for the sheath 10.

Following heating, the contents are removed from the oven, and allowed to cool. The heat shrink tube is then split from the sheath, and the mandrel is removed.

Although it is believed to be more convenient to form the liner by utilizing an inner liner that includes the heat shrink material along its entire length, this is not necessary in all instances. All that is required is that the distal, tapered portion of the liner is formed from the heat shrink material. Due to the relative configurations of the mandrel and inner liner throughout most of their respective lengths, no shrinkage of the inner liner length is typically necessary, other than at the tapered distal tip portion as described. For ease of manufacture, however, and perhaps to provide more integrity to the inner liner, it is believed more suitable to use a single heat shrinkable liner composition throughout its length.

The dimensions (for example, the thickness) of the various elements mentioned above should be selected in view of the proposed use of the introducer sheath 10. The selection of such dimensions will lie within the level of skill in the art, once benefit of the present disclosure is had. While a modest amount of trial-and-error may be needed to obtain optimal dimensions, it is believed that any required experimentation will not be undue. For example, introducer sheath 10 may be formed to have a length between about 40 and 125 cm. Generally, the lengths of inner liner 50 and outer jacket 20 are the same.

Routine additional features, such as hydrophilic coatings, radiopaque markers, side ports, etc., often provided on introducer sheaths may be incorporated in well-known fashion. In addition, the sheath can be formed by well known procedures to include one or more segments along its length that differ in flexibility from other segments. Typically, this is accomplished by forming the outer jacket of one or more segments of different durometer, generally aligned in order of decreasing durometer (e.g., increased flexibility) from the proximal end to the distal end of the sheath.

FIG. 7 illustrates a side view of the inventive introducer sheath 10 formed by the inventive process ready for insertion into a bodily passageway. Introducer sheath 10 has a tapered distal tip portion 12 that tapers to sheath distal end 14. Proximal end 15 may be flared as shown. In this figure, a conventional dilator 18 is passed through the inner diameter defined by sheath inner liner 50. Typically, dilator 18 also includes a tapered distal end 19 for ease of entry into a body opening. The transition between sheath distal end 14 and dilator 18 can be formed to have any configuration desired in order to minimize trauma to the patient upon insertion of the dilator and sheath into the body opening. Dilators for such use are well known in the medical arts, and a skilled artisan can readily select a dilator having appropriate dimensions and composition for a particular purpose.

The discussion above primarily discussed the use the heat shrinkable fluoropolymer PTFE. PTFE is commonly used in such sheaths as an inner liner composition, and therefore, it is believed that the process of the present application will have greatest application to a sheath having a PTFE liner. Nonetheless, other sheath shrinkable compositions, such as FEP (fluorinated ethylene propylene) and PFA (perfluoroalkoxy), may be appropriate for a particular use. Those skilled in the art will appreciate that when other components are used, the heat shrink temperature will be adjusted in routine fashion to account for the melt flow properties of that particular component.

The details of the construction or composition of the various elements of the introducer sheath 10 of the present invention not otherwise disclosed are not believed to be critical to the present invention, so long as the recited elements possess the strength or mechanical properties needed for them to perform as disclosed. Many such details not described herein are recited in detail in the incorporated-by-reference patent documents. Additional details of construction are believed to be well within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

The invention claimed is:

1. A method of forming an introducer sheath having a tapered distal tip portion, comprising:
    providing a mandrel having an outer configuration comprising an elongated body and a tapered distal tip;
    positioning a generally tubular inner liner over the mandrel, said inner liner comprising a heat shrinkable fluoropolymer;
    heat shrinking the inner liner over the mandrel such that said inner liner shrinks to the outer configuration of the mandrel, a distal portion of the inner liner shrinking to the configuration of the mandrel tapered distal tip and having an inner diameter substantially free of creases therealong;
    positioning a reinforcing member over a length of the inner liner;
    positioning an outer jacket over the reinforcing member and the inner liner; and
    heating an assembly comprising said inner liner, reinforcing member, and outer jacket, such that said outer jacket bonds to an outer surface of said inner liner.

2. The method of claim 1, wherein said fluoropolymer comprises heat shrinkable polytetrafluoroethylene (PTFE).

3. The method of claim 2, wherein said PTFE inner liner is heat shrunk over said mandrel at a temperature of about 650° F. (340° C.).

4. The method of claim 2, wherein said reinforcing member comprises a coil having a plurality of coil turns, and wherein said outer jacket bonds to said inner liner through said coil turns.

5. The method of claim 4, wherein said assembly is heated in a heat shrink enclosure.

6. The method of claim 5, wherein said enclosure comprises fluorinated ethylene propylene (FEP).

7. The method of claim 4, wherein said outer jacket comprises a thermoplastic material selected from the group consisting of polyether block amide, nylon, and polyurethane.

8. The method of claim 4, wherein said outer jacket comprises a plurality of jacket segments, said segments aligned in order of decreasing durometer from a proximal end to a distal end of said outer jacket.

* * * * *